(12) United States Patent
Matsui et al.

(10) Patent No.: US 7,348,158 B2
(45) Date of Patent: Mar. 25, 2008

(54) METHOD OF QUANTIFYING CHOLESTEROL IN HIGH DENSITY LIPOPROTEIN AND REAGENT COMPOSITIONS

(75) Inventors: Hiroshi Matsui, Gosen (JP); Motoko Ohta, Gosen (JP)

(73) Assignee: Denka Seiken Co., Ltd., Tokyo (JP)

( * ) Notice: Subject to any disclaimer, the term of this patent is extended or adjusted under 35 U.S.C. 154(b) by 371 days.

(21) Appl. No.: 10/502,959

(22) PCT Filed: Jan. 30, 2003

(86) PCT No.: PCT/JP03/00867

§ 371 (c)(1),
(2), (4) Date: Sep. 29, 2004

(87) PCT Pub. No.: WO03/064684

PCT Pub. Date: Aug. 7, 2003

(65) Prior Publication Data

US 2005/0095658 A1 May 5, 2005

(30) Foreign Application Priority Data

Jan. 30, 2002 (JP) ............................ 2002-022587

(51) Int. Cl.
*C12Q 1/60* (2006.01)
(52) U.S. Cl. ...................................... 435/11
(58) Field of Classification Search ...................... None
See application file for complete search history.

(56) References Cited

U.S. PATENT DOCUMENTS 4,892,815 A 1/1990 Kerscher et al.

FOREIGN PATENT DOCUMENTS

EP 0 730 028 A1 9/1996

| JP | 63-126498 A | 5/1988 |
| JP | 6-242110 A | 9/1994 |
| JP | 7-301636 A | 11/1995 |
| JP | 8-116996 A | 5/1996 |
| JP | 8-116996 A | 5/1996 |
| JP | 8-131197 A | 5/1996 |
| JP | 8-201393 A | 8/1996 |
| JP | 2001-124780 A | 5/2001 |
| JP | 2001-124780 A | 5/2001 |
| WO | 98/26090 A1 | 6/1998 |
| WO | WO-98/26090 A1 | 6/1998 |

OTHER PUBLICATIONS

Kinoshita et al. Ann Clin Biochem 1998:35:739-744.*
Okada et al. J of Clinical Laboratory Analysis 2001;15:223-229.*

* cited by examiner

*Primary Examiner*—Ralph Gitomer
*Assistant Examiner*—Bin Shen
(74) *Attorney, Agent, or Firm*—Birch, Stewart, Kolasch & Birch, LLP

(57) ABSTRACT

A method for specifically quantifying HDL cholesterol in which cholesterol in lipoproteins other than HDL is erased in the first step, and HDL cholesterol is specifically quantified in the second step, by which accurate values can be obtained even in measurements of abnormal samples such as disorder of lipid metabolism and lipoprotein abnormality, is disclosed. The method for quantifying cholesterol in high density lipoprotein according to the present invention comprises a first step of erasing cholesterol in lipoproteins other than high density lipoprotein by treating a test sample with cholesterol esterase and cholesterol oxidase in the absence of a surfactant which acts on high density lipoprotein and removing generated hydrogen peroxide; and a second step of adding a surfactant which specifically acts on high density lipoprotein to the product of said first step and quantifying hydrogen peroxide generated from cholesterol in high density lipoprotein by actions of cholesterol esterase and cholesterol oxidase. As the cholesterol oxidase used in the first step, one having a molecular weight of not more than 60 kilodaltons is used.

4 Claims, No Drawings

METHOD OF QUANTIFYING CHOLESTEROL IN HIGH DENSITY LIPOPROTEIN AND REAGENT COMPOSITIONS

TECHNICAL FIELD

The present invention relates to a method for quantifying cholesterol in high density lipoprotein (HDL) and to a reagent composition used therefor.

BACKGROUND ART

It is known that HDL relates to removal of cholesterol accumulated in cells because it receives cholesterol from various tissues including walls of blood vessels with arterial sclerosis, so that HDL is useful for estimating the risk for various arterial sclerosises including coronary artery sclerosis, and that its blood level is an indicator for the risk of onset of arterial sclerosis.

Methods for measuring cholesterol in HDL include a method in which HDL is separated from other lipoproteins by ultracentrifugation and then the HDL is measured; and a method in which the cholesterol in HDL is separated by electrophoresis, then the lipid is stained, and the intensity of the generated color is measured. However, these methods are complex or a number of samples cannot be assayed, so that they are not commonly used.

The method for measuring the cholesterol in HDL, which is generally used in the field of clinical test is the method in which a precipitating agent is added to the sample so as to coagulate the lipoproteins other than HDL, removing the coagulated lipoproteins by centrifugation, and the cholesterol in the resulting supernatant containing HDL alone is measured. Although this method is simpler than the ultracentrifugation method and the electrophoresis method, it is not satisfactorily simple because it comprises addition of the precipitating agent and subsequent separation, and a comparative large amount of sample is needed.

On the other hand, methods in which the cholesterol in HDL is separately quantified by using enzymes have been proposed. For example, a method is known, which comprises the steps of preliminarily coagulating the lipoproteins other than HDL by an antibody and polyanion, enzymatically reacting the cholesterol in HDL alone, inactivating the enzyme and simultaneously re-dissolving the coagulated mass, and measuring the absorbance of the resulting solution (Japanese Laid-open Patent Application (Kokai) No. 6-242110). However, this method has a problem in that it is necessary to add reagents at least three times, so that this method can be practiced only by the limited analyzing apparatuses. Therefore, this method is not widely used. Other methods include a method in which an enzyme reaction is carried out in the presence of a bile salt or a nonionic surfactant (Japanese Laid-open Patent Application (Kokai) No. 63-126498); a more recently developed method in which the cholesterol in HDL is specifically trapped by chemically modified cholesterol esterase and/or cholesterol oxidase in the presence of a clathrate compound such as cyclodextrin (Japanese Laid-open Patent Application (Kokai) No. 7-301636); and a method in which the lipoproteins other than HDL are made into aggregates or complexes and then the cholesterol in HDL is trapped by an enzyme reaction (Japanese Laid-open Patent Application (Kokai) Nos. 8-131197 and 8-201393). However, with these methods, the results for certain samples are different from the results by the precipitation method, so that their specificities are problematic.

The present applicant previously developed a method for quantifying HDL cholesterol which does not necessitate a fractionating operation (International Publication No. WO98/26090), and the reagent therefor is now being generally used in the actual clinical tests. In this method, cholesterol in lipoproteins other than HDL in a sample is erased (the term "erase" herein means to decompose ester type cholesterol and free cholesterol, and to make the decomposed products undetectable in the second step), and HDL cholesterol is specifically quantified in the second step.

However, this method has a problem in that the measured amount of HDL is larger than the actual amount of HDL for abnormal clinical samples such as disorder of lipid metabolism and lipoprotein abnormality. Abnormal samples often indicate abnormal triglyceride (TG) values, bilirubin values and the like in biochemical tests, so that overcoming the above-mentioned problem will increase the usefulness of the measuring method, and so the solution of the problem is demanded.

DISCLOSURE OF THE INVENTION

Accordingly, an object of the present invention is to provide a method for quantifying HDL cholesterol in which cholesterol in lipoproteins other than HDL is erased in the first step, and HDL cholesterol is specifically quantified in the second step, by which accurate values can be obtained even in measurements of abnormal samples such as disorder of lipid metabolism and lipoprotein abnormality.

The present inventors investigated the cause of the positive error of measurement to discover that, with the abnormal samples, the cholesterol in the lipoproteins other than HDL is not well erased in the first step, and the cholesterol is carried over to the HDL-specific reaction in the subsequent second step, thereby giving a positive influence to the reaction of HDL.

Thus, the present inventors studied the method for increasing the degree of erasing in the first step to discover that the degree of erasing of cholesterol in the lipoproteins other than HDL is increased by using a cholesterol oxidase having a small molecular weight in the first step.

More particularly, lipoprotein particles are formed by aggregation of ester type cholesterol, free cholesterol, TG (triglyceride), phospholipids and proteins.

Each particle has a structure in which proteins and phospholipids exist at the surface of the particle, free cholesterol exists therein, and ester type cholesterol and TG exist at the center. By applying a cholesterol oxidase having a small molecular weight to the lipoproteins, the cholesterol oxidase can enter the inside of the lipoproteins other than HDL and reacts with free cholesterol existing near the surface to change the particle structure, so that cholesterol esterase also acts on the ester type cholesterol, thereby promoting the erasing reaction. In this case, since HDL is a high density lipoprotein and the percentage of proteins at the surface is high, the low molecular cholesterol oxidase cannot enter the inside of the particle, so that the reaction does not occur.

That is, the present invention provides a method for quantifying cholesterol in high density lipoprotein, comprising a first step of erasing cholesterol in lipoproteins other than high density lipoprotein by treating a test sample with cholesterol esterase and cholesterol oxidase in the absence of a surfactant which acts on high density lipoprotein and removing generated hydrogen peroxide; and a second step of adding a surfactant which specifically acts on high density lipoprotein to the product of the first step and quantifying hydrogen peroxide generated from cholesterol in high density lipoprotein by actions of cholesterol esterase and cholesterol oxidase; characterized in that the cholesterol oxidase used in the first step has a molecular weight of not more than 60 kilodaltons. The present invention also provides a reagent composition for quantifying cholesterol in high density lipoprotein, which is used for the first step of the above-described method according to the present invention, which comprises the cholesterol esterase, the cholesterol oxidase having a molecular weight of not more than 60 kilodaltons and a component which removes hydrogen peroxide.

By the method of the present invention, in a method for measuring HDL in a test sample containing HDL and other lipoproteins such as LDL, VLDL and CM, HDL may be selectively, simply and accurately quantified even when the sample is an abnormal test sample such as high TG or one from a patient suffering from a hepatic disorder (high bilirubin).

BEST MODE FOR CARRYING OUT THE INVENTION

Cholesterols contained in lipoproteins include ester type cholesterol (cholesterol ester) and free cholesterol. In this specification, the term "cholesterol" includes both of these unless otherwise specified.

The test sample subjected to the method of the present invention may be any sample which may contain lipoproteins such as HDL, LDL, VLDL and CM.

Examples of the test samples include body fluids such as blood, sera and plasma as well as dilutions thereof, although the test samples are not restricted thereto. The method of the present invention is particularly useful when the test sample is an abnormal sample such as a blood sample containing TG at a level of not less than 400 mg/dL, particularly not less than 1000 mg/dL, or containing bilirubin at a level of not less than 2.00 mg/dL, particularly not less than 3.00 mg/dL. These values are blood levels of non-diluted blood. As mentioned above, by the known method, there is a problem in that the determined amount of HDL, which is often measured for samples containing high TG or high bilirubin, is higher than the actual amount of the HDL. As will be concretely shown in Examples below, by the method of the present invention, the amount of HDL can be accurately measured even when the sample is a blood sample containing high TG or high bilirubin. It should be noted that "blood sample" herein includes whole blood, serum and plasma, as well as dilutions thereof.

The method of the present invention comprises a first step and a second step. In the first step, the cholesterol in LDL, VLDL and CM is erased in the absence of a surfactant which acts on HDL. In the subsequent second step, cholesterol is quantified using a surfactant specific to HDL. As the cholesterol oxidase used in the first step, one having a low molecular weight is used.

The term "erase" in the first step means to decompose cholesterol, and to make the decomposed products undetectable in the second step. The methods for selectively erasing the cholesterol in the lipoproteins other than HDL, that is, in LDL, VLDL, CM and the like include the following methods.

That is, cholesterol esterase and cholesterol oxidase are acted on the test sample in the absence of a surfactant which acts on HDL, and the generated hydrogen peroxide is removed. By the action of cholesterol esterase, the ester type cholesterol in the lipoproteins are hydrolyzed to yield free cholesterol and fatty acids. The thus generated free cholesterol and the free cholesterol inherently existing in the lipoproteins are oxidized by the action of cholesterol oxidase to yield cholestenone and hydrogen peroxide. The thus generated hydrogen peroxide is removed.

Methods for removing hydrogen peroxide include a method in which the hydrogen peroxide is decomposed to water and oxygen by catalase; and a method in which a phenol-based or aniline-based hydrogen donor compound, such as DAOS(N-ethyl-N-(2-hydroxysulfopropyl)-3,5-dimethoxyaniline), which reacts with hydrogen peroxide to yield a colorless quinone, is reacted with the hydrogen peroxide to convert the hydrogen peroxide to the colorless quinone, although the methods for removing hydrogen peroxide are not restricted to these methods.

In the above-mentioned first step, by treating the sample with the low molecular cholesterol oxidase in the absence of a surfactant which acts on HDL, the cholesterol in HDL is not substantially reacted, while the cholesterol in the other lipoproteins such as LDL, VLDL and CM are reacted and erased. By this, in the subsequent second step, the cholesterol in HDL is selectively quantified.

The molecular weight of the cholesterol oxidase used in the first step is 20 kDa to 60 kDa, preferably 30 kDa to 40 kDa. The cholesterol oxidase having a molecular weight within this range, which is used in the method of the present invention, may be obtained from various microorganisms such as bacteria and yeasts, and its origin is not restricted at all. Further, since such a cholesterol is commercially available, a commercially available one may be employed. In the known methods for measuring HDL, high molecular cholesterol oxidases having molecular weights of more than 60 kilodaltons have been employed.

The concentration of the cholesterol esterase in the reaction mixture in the first step may preferably be about 0.2 to 2.0 U/mL, and cholesterol esterases produced by bacteria belonging to genus *Pseudomonas* are effective. The concentration of the cholesterol oxidase may preferably be about 0.1 to 1.5 U/mL.

In cases where catalase is used as a component for removing hydrogen peroxide, the concentration of the catalase may preferably be about 50 to 2000 U/mL. The concentration of the peroxidase used for converting hydrogen peroxide to colorless quinone may preferably be about 0.4 to 1.0 U/mL. The concentration of the phenol-based or aniline-based hydrogen donor compound may preferably be about 0.4 to 2.0 mmol/L.

The reaction in the first step is carried out in a buffer with a pH of 5 to 8. The buffer may preferably be phosphate buffer, glycine buffer, Tris buffer or Good's buffer. Especially, Bis-Tris, PIPES, MOPSO, BES, HEPES and POPSO which are Good's buffer are preferred. The concentration of the buffer may preferably be about 10 to 500 mM.

A lipoprotein hydrolase may optionally be added to the reaction mixture in the first step. Addition of this enzyme is preferred because especially the cholesterol in VLDL easily reacts. The concentration of this enzyme in the reaction mixture may preferably be about 5.0 to 10.0 U/mL. Further, the reaction solution in the first step may optionally contain a surfactant which does not substantially act on HDL and/or other component(s) such as clathrate compounds including cyclodextrin, in (an) amount(s) not adversely affecting the effect of the present invention.

The reaction temperature in the first step may preferably be about 25° C. to 40° C., and 37° C. is most preferred. The reaction time may be about 2 to 10 minutes.

In the following second step, a surfactant which specifically acts on HDL is added to the reaction product of the first step, and the cholesterol in high density lipoprotein is enzymatically quantified. The term "surfactant which specifically acts on HDL" means a surfactant by which the cholesterol in HDL reacts due to the action of enzymes such as cholesterol esterase and cholesterol oxidase (the reaction ratio is not less than 70%, preferably not less than 90%), while the cholesterol in the lipoproteins other than HDL does not substantially react (the reaction ratio is not more than 30%, preferably not more than 20%). The hydrophilicity lipophilicity balance (HLB) of the surfactant used here is 13 to 14. As the surfactant, nonionic surfactants are preferred, and polyalkylene oxide derivatives are especially preferred. Among the polyalkylene oxide derivatives, polyethylene oxide derivatives are most preferred. The above-mentioned range of HLB may be attained by mixing a plurality of surfactants, and such a mixture of a plurality of surfactants may also be used. The method for calculating HLB of surfactants is well-known, and is described in, for example, Hiroshi HORIGUCHI, "New Surfactants", 1986, Sankyo Shuppan.

Preferred specific examples of the surfactant include polyoxyethylene lauryl ether, polyoxyethylene cetyl ether, polyoxyethylene oleyl ether, polyoxyethylene higher alcohol (C4-C35) ether, polyoxyethylene octyl phenyl ether, polyoxyethylene nonylphenyl ether, polyoxybenzylphenyl ether and the like, although the surfactant is not restricted thereto.

Although the concentration of the surfactant in the second step is not restricted, it may preferably be 0.05 to 3% by weight, more preferably 0.1 to 1.5% by weight based on the total reaction mixture.

In the presence of the above-mentioned surfactant, the HDL cholesterol in the test sample may be enzymatically quantified. That is, in the first step, most of the cholesterol in the lipoproteins other than HDL is erased, and with the synergistic effect with the reaction in the second step, the cholesterol in HDL alone is quantified.

The method for enzymatically quantifying cholesterol per se is well-known in the art. For example, as in the first step, cholesterol is quantified by generating hydrogen peroxide from cholesterol ester and free cholesterol by the actions of cholesterol esterase and cholesterol oxidase, and by quantifying the generated hydrogen peroxide. Quantification of hydrogen peroxide may be carried out by, for example, reacting the hydrogen peroxide with a compound which forms a quinone pigment, and by measuring the amount of the generated quinone pigment by measuring absorbance or the like. The quinone pigment may be formed by, for example, reacting hydrogen peroxide and 4-aminoantipyrine and DAOS or HDAOS (N-(2-hydroxysulfopropyl)-3,5-dimethyoxyaniline). The quinone pigment formed thereby has the maximum absorbance at 593 nm when DAOS is used, and has the maximum absorbance at 583 nm when HDAOS is used. Although the concentration of the compound which yields the quinone pigment is not restricted, the concentration of 4-aminoantipyrine, for example, may preferably be 0.1 to 2.0 mM, more preferably 0.5 to 1.5 mM, and the concentration of DAOS or HDAOS may preferably be 0.1 to 1.5 mM, more preferably 0.4 to 1.0 mM. Although the concentration of the peroxidase is not restricted, it may preferably be 0.4 to 5 U/mL in the total reaction mixture. Preferred reaction conditions (reaction temperature, reaction time, buffer and pH) are the same as the preferred reaction conditions in the first step.

In cases where the generated hydrogen peroxide is decomposed with catalase, a catalase inhibitor such as sodium azide is used in the second step so as to inhibit the catalase because it is necessary to inhibit the catalase in the second step.

The present invention also provides a reagent composition for quantifying cholesterol in high density lipoprotein, which is used for the first step of the method of the present invention, which comprises cholesterol esterase, cholesterol oxidase having a molecular weight of not more than 60 kilodaltons and a component which removes hydrogen peroxide. As the component which removes hydrogen peroxide, as mentioned above, (1) catalase or (2) phenol-based or aniline-based hydrogen donor compound and peroxidase, or the like may be employed. The ratio of the components in the reagent composition is the ratio with which the above-mentioned concentrations are attained when used. The reagent composition may further comprise the above-mentioned buffer agent and/or the lipoprotein hydrolase.

The present invention will now be described more concretely by way of examples thereof. It should be noted, however, the present invention is not restricted to the examples below. In the examples below, all "%" are by weight unless otherwise specified.

REFERENCE EXAMPLE

Using samples containing known amounts of purified HDL, LDL, VLDL and CM, respectively, the cholesterol in each of the lipoproteins was enzymatically quantified in the presence of a nonionic surfactant Emulgen 911 (polyoxyethylene nonyl ether, HLB 13.7), Emulgen B66 (polyoxyethylene derivative, HLB 13.2) or a mixture of Emulgen B66 and Emulgen A90 (polyoxyethylene derivative, HLB 14.5), all of which are commercially available from KAO CORPORATION. This operation was carried out as follows.

To a solution containing 0.5 U/mL of cholesterol esterase, 0.4 U/mL of cholesterol oxidase, 0.5 U/mL of peroxidase, 1.0 mmol/L of 4-aminoantipyrine and 0.5 mmol/L of HDAOS in 50 mM PIPES buffer, pH 7.0, Emulgen 911 or Emulgen B66 was added to a concentration of 0.1% by weight, or Emulgen B66/Emulgen A90 mixture (9/1) was added to a concentration of 1.3% by weight. Twenty microliters of each sample was mixed with 2.0 mL of the thus prepared reagent and the resulting mixture was allowed to react at 37° C. for 10 minutes, followed by measuring absorbance at 600 nm.

As a result, the reaction ratio (i.e., the ratio of the quantified cholesterol in the total cholesterol) was about 95% for the cholesterol in HDL, and about 18 to 22% for the cholesterols in other lipoproteins.

From this, it can be seen that Emulgen 911, Emulgen B66 and the Emulgen B66/Emulgen A90 mixture are within the scope of the term "surfactant which specifically acts on high density lipoprotein".

EXAMPLE 1

Three types of reagents having the following compositions were prepared:

In the three types of reagents, only the molecular weight of cholesterol oxidase was different, and all of the other components were the same.

Common Components

First Reagent

| | |
|---|---|
| BES buffer, pH 7.0 | 100 mmol/L |
| HDAOS | 0.7 mmol/L |
| Cholesterol esterase | 1.5 U/mL |
| Catalase | 80 U/mL |

Second Reagent

| | |
|---|---|
| BES buffer, pH 7.0 | 100 mmol/L |
| 4-aminoantipyrine | 4.0 mmol/L |
| Peroxidase | 4.0 U/mL |
| Sodium azide | 0.1% |
| Emulgen B66 (HLB13.2) commercially available from KAO CORPORATION | 1.3% |

Reagent

One of cholesterol oxidases (CO) having different molecular weights was added to the first reagent of each reagent to a concentration of 0.8 U/mL.

Reagent 1

High molecular CO (trademark: CON II, commercially available from Asahi Kasei Corporation, molecular weight: 61.8 kDa)

Reagent 2

Low molecular CO (trademark: COO-321, commercially available from Toyobo Co., Ltd., molecular weight: 55.0 kDa)

Reagent 3

Low molecular CO (trademark: CO, commercially available from Asahi Kasei Corporation, molecular weight: 38.0 kDa)

Reagent 4

Low molecular CO (trademark: COO-311, commercially available from Toyobo Co., Ltd., molecular weight: 34.0 kDa)

To 4 μL of each of the samples (sera) from healthy individuals, samples of high TG and samples of high bilirubin (BIL), 300 μL of the above-described first reagent preliminarily warmed at 37° C. was added and the mixture was allowed to react at 37° C. for 5 minutes. Then 100 μL of the second reagent was added and the mixture was allowed to react at 37° C. for 5 minutes, followed by measurement of absorbance at 600 nm of the reaction solution. On the other hand, the amounts of HDL cholesterol in the same samples were determined by the ultracentrifugation method described in "New Biochemistry Experiments Lecture", vol. 4, Lipid I, Triglycerides and Lipoproteins", 181 (1993). The percentage of the difference between the value determined by using each reagent and the value determined by the ultracentrifugation method was calculated.

$(A-B)/B \times 100$ (wherein A represents the value obtained by using each reagent, and B represents the value obtained by the ultra-centrifugation method).

The concrete methods for measuring the TG value and the BIL value were as follows:

As the method for measuring TG value, the LPL-GK-GPO-based enzyme method described in "Clinical Test Handbook, vol. 31", 559 (1998) was employed. The BIL value was measured by the Michaelsson's modified method which is a modification of Jendrassik-Grof method described in "Clinical Test Handbook, vol. 31", 559 (1998).

The results are shown in Tables 1 to 3. The values in the parentheses indicate the percentage of the difference from the value obtained by the ultracentrifugation method, which percentage was calculated by the above-described equation.

TABLE 1

Samples from healthy individuals

| | Ultra-centrifugation Method | Reagent 1 | Reagent 2 | Reagent 3 | Reagent 4 |
|---|---|---|---|---|---|
| 1 | 45.0 | 45.3(0.7) | 44.2(−1.8) | 45.3(0.7) | 44.9(−0.2) |
| 2 | 53.4 | 54.0(1.1) | 54.5(2.1) | 53.7(0.6) | 54.1(1.3) |
| 3 | 66.7 | 66.6(−0.1) | 66.5(−0.3) | 66.4(−0.4) | 66.8(0.1) |
| 4 | 78.3 | 77.8(−0.6) | 79.3(1.3) | 78.5(0.3) | 78.6(0.4) |
| 5 | 85.7 | 86.4(0.8) | 85.3(−0.5) | 85.9(0.2) | 85.9(0.2) | unit: mg/dL (difference: %)

TABLE 2

Samples of high TG values

| | Ultracentrifugation Method | Reagent 1 | Reagent 2 | Reagent 3 | Reagent 4 |
|---|---|---|---|---|---|
| 1 (TG value 1230) | 43.0 | 47.8(11.2) | 44.9(4.4) | 42.9(−0.2) | 43.0(0.0) |
| 2 (TG value 1560) | 30.3 | 35.0(15.5) | 31.7(4.6) | 29.7(−2.0) | 29.8(−1.7) |
| 3 (TG value 1870) | 36.0 | 38.7(7.5) | 36.7(1.9) | 35.9(−0.3) | 36.0(0.0) |
| 4 (TG value 2040) | 24.6 | 26.9(9.3) | 25.8(4.9) | 25.0(1.6) | 24.8(0.8) |
| 5 (TG value 2600) | 33.2 | 35.2(6.0) | 34.1(2.7) | 33.4(0.6) | 33.2(0.0) | unit: mg/dL (difference: %)

TABLE 3

Samples of high BIL values

| | Ultracentrifugation Method | Reagent 1 | Reagent 2 | Reagent 3 | Reagent 4 |
|---|---|---|---|---|---|
| 1 (BIL value 3.3) | 60.1 | 70.1(16.6) | 65.8(9.5) | 61.9(3.0) | 60.5(0.7) |
| 2 (BIL value 5.6) | 14.2 | 22.4(57.7) | 15.7(10.6) | 13.9(−2.1) | 13.8(−2.8) |
| 3 (BIL value 8.2) | 13.1 | 36.4(178) | 19.4(48.1) | 12.2(−6.9) | 12.3(−6.1) |
| 4 (BIL value 12.4) | 10.6 | 20.1(89.6) | 11.8(11.3) | 9.8(−7.5) | 9.6(−9.4) |
| 5 (BIL value 16.8) | 5.2 | 16.2(212) | 9.9(90.4) | 5.2(0.0) | 5.1(−1.9) | unit: mg/dL (difference: %)

As shown in Table 1, for the samples from healthy individuals, values similar to the values determined by the ultracentrifugation method were obtained when any of the reagents was used, while for the high TG or high BIL samples, the values obtained by using a low molecular cholesterol oxidase was closer to the values obtained by the ultracentrifugation method.

The invention claimed is:

1. A method for quantifying cholesterol in high density lipoprotein, which comprises: (a) erasing cholesterol in lipoproteins other than high density lipoprotein by treating a test sample with cholesterol esterase and low molecular weight cholesterol oxidase in the absence of a surfactant which acts on high density lipoprotein and removing generated hydrogen peroxide; (b) adding a surfactant which specifically acts on high density lipoprotein to the product of step (a), and (c) quantifying hydrogen peroxide generated from cholesterol in the high density lipoprotein of step (b) by actions of cholesterol esterase and low molecular weight cholesterol oxidase; wherein said low molecular weight cholesterol oxidase has a molecular weight of not more than 55.0 kilodaltons.

2. The method according to claim 1, wherein said low molecular weight cholesterol oxidase has a molecular weight of 30 to 40 kilodaltons.

3. The method according to claim 1 or 2, wherein said surfactant which specifically acts on the high density lipoprotein has an hydrophilicity-lipophilicity balance (HLB) value of 13 to 14.

4. The method according to claim 3, wherein said surfactant which specifically acts on the high density lipoprotein is a polyalkylene oxide derivative.

* * * * *